United States Patent [19]

Peyman et al.

[11] Patent Number: 5,346,689
[45] Date of Patent: Sep. 13, 1994

[54] METHOD OF PERFORMING ANGIOGRAPHY

[76] Inventors: Gholam A. Peyman; Bahram Khoobehi, both of 2020 Gravier St., Ste. B, New Orleans, La. 70112-2234

[21] Appl. No.: 111,294

[22] Filed: Aug. 24, 1993

Related U.S. Application Data

[60] Division of Ser. No. 880,301, May 9, 1992, Pat. No. 5,266,302, which is a continuation of Ser. No. 592,190, Oct. 3, 1990, abandoned.

[51] Int. Cl.$^5$ ............................................. A61K 49/00
[52] U.S. Cl. ........................................ 424/7.1; 424/4; 424/9; 128/654; 514/453; 514/411
[58] Field of Search ................ 424/9, 7.1, 4; 514/453, 514/411; 128/654

[56] References Cited

PUBLICATIONS

Fang et al. "Comparative Study of Three Fluorescent Dyes for Angiography . . . " Ophthalmic Surgery, vol. 21(4), Apr. 1990, pp. 250-257.

*Primary Examiner*—Gary E. Hollinden
*Assistant Examiner*—John D. Pak
*Attorney, Agent, or Firm*—Haverstock, Garrett & Roberts

[57] ABSTRACT

A method of performing angiography of the occular fundus of an eye of a patient includes the steps of injecting intravenously calcein into the patient in an effective amount immediately prior to angiography and performing angiography on the patient. The invention further discloses a method of performing photocoagulation therapy and/or photodynamic therapy and angiography of the occular fundus of an eye of a patient which includes the steps of performing photocoagulation therapy, injecting intravenously calcein into the patient in an effective amount immediately prior to angiography, and performing angiography on the patient.

7 Claims, No Drawings

METHOD OF PERFORMING ANGIOGRAPHY

"This is a divisional of copending application Ser. No. 07/880,301 filed on May 9, 1992, which was a continuation of application Ser. No. 07/592,190 filed on Oct. 3, 1990, now abandoned."

BACKGROUND OF THE INVENTION

The present invention relates to a method of performing angiography by using calcein as the fluorescent indicator substance and also to a method of performing photocoagulation therapy and angiography.

Photography of the circulatory system of the eye and angiography of the ocular fundus require the absorption of a fluorescent indicator substance or dye into the blood as it flows through the vasculature of the eye. Investigators have reported the use of soduim fluorescein (Naf), carboxyfluorescein (CF), indocyanine green, lissamine green, patent blue, Evans blue, and acridine orange as dyes suitable for angiography. Fluorescein angiography is one of the most improtant tools in diagnosing retinal-chloroidal diseases. Sodium fluorescein and indocyanine green are the two agents currently used as indicators for angiography of the retinal and choroidal vasculature. Sodium fluorescein is the only fluorescent dye currently in clinical use.

Sodium fluorescein has its light absorption peak near 490 nm and it fluoresces maximally at 514 nm to 520 nm. The molecular weight of sodium fluorescein is 376 and it has a relatively high lipid solubility. Sodium fluorescein is readily metabolized to fluorescein glucuronide, which is weakly fluorescent and easily crosses the blood-ocular barrier. Given these factors, angiograms taken with sodium fluorescein have a relatively short decay time in the retinal vasculature. Also, with sodium fluorescein, fluorescein leakage into the vitreous tends to obscure retinal and choroidal structures in later phases which hinders or prohibits photocoagulation therapy prior to or after angiography.

Carboxyfluroescein is another fluorescent dye which has been used for fundus angiography. Carboxyfluorescein is a hydrophilic derivative of fluorescein. The light absorption peak of carboxyfluorescein is 490 nm and it fluoresces maximally at 520 nm. Carboxyfluorescein has a molecular weight of 373. The main distinction between carboxyfluorescein and sodium fluorescein is that carboxyfluorescein has 1/1000 the lipid solubility of sodium fluorescein and thus is less likely to penetrate cell membranes. Studies of carboxyfluroescein used in fluorophotometry to investigate blood-ocular barriers indicate that it may delineate certain abnormalities of these barriers better than sodium fluorescein. Because carboxyfluorescein is not as readily glucuronated as sodium fluorescein, carboxyfluorescein also has been used as a tracer in quantitative physiological studies of the anterior chamber of human eyes.

Although sodium fluorescein and carboxyfluorescein are suitable for angiography there is a need for a fluorescent dye which has a longer circulation decay time than that of these and any other known fluorescent indicator. Additionally, there is a need for a fluorescent dye which has limited leakage to permit simultaneous angiography and photocoagulation therapy without obscuring the fundus view with leaking dye from the photocoagulated structure.

SUMMARY OF THE INVENTION

In order to increase the circulation decay time and to permit simultaneous angiography and photocoagulation therapy a method of performing angiography is provided which includes injecting intravenously calcein into the patient and performing angiography on the patient. The method of the present invention also allows laser photocoagulation therapy to be performed prior to angiography when calcein is used as the fluorescent dye.

The flourescent indicator substance to be used in the method of performing angiography of the present invention is calcein. Calcein is a water-soluble, self-quenching compound that is inexpensive, stable, and highly fluorescent. Calcein is prepared by the interaction of fluorescein, formaldehyde and iminodiacetic acid. The resulting compound has the structure:

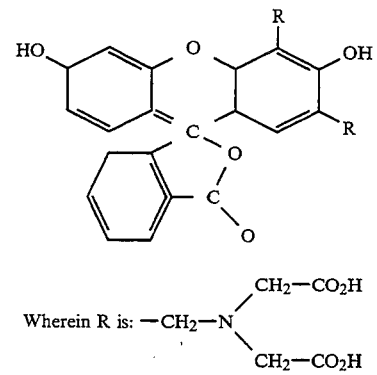

Wherein R is: $-CH_2-N\begin{matrix}CH_2-CO_2H\\CH_2-CO_2H\end{matrix}$

Calcein has a maximum abxorption occurring at 495 nm and maximum emission at 515 nm. Calcein has a molecular weight of 622 and a lipid solubility that is less than that of sodiuum fluorescein. Calcein is a highly negatively charged molecule in neutral pH and does not easily leave the wall of the blood vessel. A detailed description of the properties of calcein can be found in Diehl, *Calcein, Calmagite and O-O'-dihydroxyazobenzene: Titrimetric, Colormetric and Fluorometric Reagents for Calcium and Magnesium*, G. Frederick Smith Chemical Company, Columbus, Ohio, 1964.

Accordingly, it is an object of the invention to provide a method which permits simultaneous photocoagulation therapy and angiography to be performed.

It is a further object of the present invention to use calcein in a method of performing angiography of the ocular fundus of the eye.

These and other objects and advantages of the present invention will become apparent to those skilled in the art after considering the following detailed specification.

DETAILED DESCRIPTION OF PREFERRED EMBODIMENTS

The following sets forth summaries of a number of laboratory and animal studies which demonstrate the principles of the present invention, namely, that use of calcein as the fluorescent dye in angiography provides unexpected results because calcein has a longer decay time than other dyes used for this purpose and the use of calcein as the fluorescent dye in angiography after photocoagulation therapy provides unexpected results because calcein has less leakage or staining than other dyes used for this purpose. The laboratory and animal studies discussed herein have been described in articles by the inventors herein which have appeared in Ophthalmic Surgery, April 1990, Vol. 21, No. 4, pages 250–257 and International Ophthalmology 14: 245–250, 1990, with both articles being incorporated herein by this reference.

Calcein to be used as fluorescent dye for fundus angiography was obtained from Sigma Chemical Company, St. Louis, Mo. The calcein is repurified by column chromatography. The method for repurifying calcein comprises the following steps. A 10 ml of 100 mg/ml solution of calcein, having a pH of between 7.4 and 7.6, is applied to a 2.5×40 cm column packed with Sephadex LH-20 to remove any hydrophobic impurities. Distilled, deionized water is used to elute the dye at a flow rate of 1.0–1.2 ml/min. After elution, fractions of approximately 2.0 ml are collected and the clear deep red fractions are combined. The fractions that preceded and followed the deep red fractions contained brown and green contaminants are discarded. After the deep red fractions are combined, the concentration of the combined fractions is determined by measurement of the absorption at 495 nm of aliquots of the dye diluted in methanol. The concentration of the dye is then adjusted to 50 mg/ml.

Three experiments were performed using monkeys and rabbits. The first experiment consisted of performing normal angiography in monkeys. The second experiment consisted of performing normal angiography in rabbits. The third experiment consisted of performing angiography in rabbits after laser photocoagulation of the eyes of the rabbits. Although laser photocoagulation therapy is described, it is also possible to perform photodynamic therapy. Photodynamic therapy includes injecting a dye into the eye and using a laser, such as a red or infrared laser, directed at the eye for the dye inside the eye to absorb the laser energy. It is to be understood that laser photocoagulation therapy includes photodynamic therapy. Two squirrel monkeys weighing 595 g and 620 g, respectively and six pigmented rabbits weighing from 1,265 g to 2,050 g were used in the experiments. A mixture of ketamine hydrochloride (30 mg/kg body weight) and xylazine (3 mg/kg body weight) was used for intramuscular anesthesia. Proparacaine hydrochloride 0.5% was instilled into the eye prior to laser treatment. The pupils were dilated using phenylephrine hydrochloride 10%, tropicamide 1.0%, and cyclopentolate hydrochloride 0.5%. Sodium fluorescein was prepared from Fluorescite obtained from Alcon Laboratories of Fort Worth, Tex. Carboxyfluorescein was obtained from Molecular Probes of Eugene, Oreg. Calcein was obtained from Sigma Chemical Company of St. Louis, Mo. The sodium fluorescein and carboxyfluorescein were purified by column chromatography according to a method reported by Ralston et al. in Biochim biophys Acta. 1981;649:133–137. The concentrations used in the experiments were sodium fluorescein 7 mg/ml, carboxyfluorescein 7 mg/ml, and calcein 11.3 mg/ml. All of the dyes had a molarity of 18 mM. One ml/kg of each dye was injected into the ear vein in the rabbits and into the leg vein in the monkeys.

The following equipment was utilized for the experiments. Fundus angiograms were taken using a Topcon fundus camera, Model TRC-WT. Although a fundus camera was used, a video camera may also be used. Filter devices were used for routine fluorescein angiography. Transmittance of these filters was measured using a spectrophotometer, such as Model DU40 manufactured by Beckman of Fullerton, Calif. A flash intensity of 25 was used for the rabbits and a flash intensity of 300 was used for the monkeys. Kodak TRI-X film (ASA 400) was used. All films were developed with identical processes. Fundus photocoagulation was performed using a Coherent Model920 laser which is an argon-blue green laser. Other lasers having other frequencies, such as red or infrared, may also be used. In all experiments at least 72 hours elapsed before angiography was repeated in any one animal.

The first experiment, as previously discussed, consisted of performing normal angiography of monkeys. Angiography was performed following the administration of an intravenous injection of one of the three dyes, sodium fluorescein, carboxyfluorescein, and calcein. After injection sequential photographs of the fundus were taken every few seconds during the first minute, the 2, 3, 5, 10, 15, 20, 30, 45, 60, 75, and 90 minutes.

The second experiment, as discussed above, consisted of performing normal angiography of rabbits. The procedure was similar to that of the first experiment. Angiograms were taken at the same intervals up to and including the one done 60 minutes after injection. Then photographs were taken up to 4 hours after injection.

The third experiment consisted of performing angiography of rabbits after laser photocoagulation of the eyes of the rabbits. Three rabbit eyes were used for this experiment. Each eye was photocoagulated in two different areas. The first area had multiple laser lesions created close to the optic disc in an attempt to occlude the major retinal vessels. The laser spot size was 200 micrometers, the power was 500 to 600 mW, and the exposure time was 200 ms. The second area consisted of a group of 16 to 20 lesions of 200 micrometers apart. The power ranged from 120 to 200 mW and the exposure duration was 200 ms. This resulted in a homogenous whitish-yellow lesion. Thirty minutes after laser photocoagulation angiography was performed as in the second experiment.

The results of the three experiments are as follows. Anglograms in the first experiment (normal angiography in monkeys) taken 17 seconds after the injection of sodium fluorescein showed a choroidal flush that became very bright and somewhat diminished visualization of the overlying retinal vessels. The choroidal flush was less intense with carboxyfluorescein and calcein which provided better contrast for visualization of the retinal vascular tree. Three minutes after injection the intensity of the choroidal flush was reduced in the eyes injected with sodium fluorescein and carboxyfluorescein. The choroidal flush in the eyes injected with calcein was practically invisible at three minutes after injection. Retinal circulation was barely visible in any of the angiograms taken after 10 minutes, regardless of the dye used. Sixty minutes after injection the angiograms taken with sodium fluorescein were completely dark. However, some fluorescence still could be seen in the retina vessels in the angiograms taken with carboxyfluorescein and calcein.

In the second experiment (normal angiography in rabbits) the choroidal flush in the early phase of angiography (0 to 25 seconds) was most intense in soduim fluorescein injected eyes, less intense with carboxyfluorescein injected eyes, and least intense with calcein injected eyes. One minute after injection all dyes provided good visualization of the retinal and choroidal vasculature. The intensity of choroidal fluorescence in the sodium fluorescein injected eyes diminished only after five minutes, whereas it diminished after 16 seconds with carboxyfluorescein, and after 43 seconds with calcein. In the rabbits there was no difference in the circulation decay times of the three dyes.

In the third experiment (angiography after laser photocoagulation) angiograms taken from 22 to 33 seconds after dye injection showed more intense leakage around the occluded vessels (the first area) in the sodium fluorescein and the carboxyfluorescein injected eyes than in those injected with calcein. In the calcein injected eyes it was possible to detect the occluded vessel. Ten minutes after injection a significant amount of dye leakage occurred in the first area of the sodium fluorescein injected eyes. In the carboxyfluorescein and calcein angiograms leakage was present but was less intense than it was in the sodium fluorescein angiograms. Angiograms of fresh lesions of the periphery of the retina (the second area) taken at 30 minutes after injection showed that soduim fluorescein had leaked into the tissues and it was difficult to visualize individual laser lesions. Similar changes occurred with carboxyfluorescein but to a lesser degree. With calcein, the dye staining in the photocoagulated area was minimal and individual lesions could be visualized distinctly.

The experiments also showed that when calcein was injected into the anesthetized monkeys there was no injection reaction nor were acute toxic effects observed in the monkeys after repeated injections. Other experiments have been performed on rats in which a dosage at or below 170 mg/kg of calcein was found to be non-toxic.

The above-described studies and experiments have shown that the method of performing angiography on the eye by injecting intravenously calcein into the patient overcomes the disadvantages of the more commonly used fluorescent indicator dyes. These experiments demonstrate the distinct characteristics found in angiograms which use calcein as the fluorescent indicator substance. Calcein has been shown to have a longer circulation decay time which permits detailed visualization of the retinal vasculature in the early phase of angiography. Additionally, calcein was shown to reduce leakage and staining of tissues immediately after photocoagulation therapy.

Calcein preferably may be used alone or may be used in combination with other dyes in combination with performing angiography. Enough calcein must be used to effectively extend the time for circulation decay to render the dye effective and too much calcein may have harmful side effects. The amount of calcein used in this invention will depend on the body weight of the mammal on which angiography is being performed. The calcein will be injected in a water solution which may or may not include other dyes. An effective amount of calcein will generally be at least 5 mg of calcein per kg of mammal body weight. Preferably, about 7 mg of calcein per kg of mammal body weight will be optimum.

There has thus been shown and described a novel method of performing angiography which fulfills all of the objects and advantages sought therefor. It will be apparent to those skilled in the art, however, that many changes, modifications, variations, and other uses and applications of the subject method of performing angiography are possible and contemplated. All such changes, modifications, variations, and other uses and applications which do not depart from the spirit and scope of this invention are deemed to be covered by the invention, which is limited only by the claims which follow.

What is claimed is:

1. A method of performing photocoagulation therapy and angiography of the ocular fundus of an eye of a patient comprising the steps of:
   performing photocoagulation therapy on the eye of the patient;
   injecting intravenously a solution of purified calcein into the patient in an effective amount immediately prior to angiography; and
   performing angiography on the patient.

2. The method of claim 1 wherein the step of performing angiography comprises the step of using a fundus or video camera.

3. The method of claim 1 wherein the calcein is purified by performing column chromatography.

4. The method of claim 1 wherein the performing photocoagulation therapy step comprises using a laser.

5. The method of claim 4 wherein the laser is an argon-blue green laser.

6. The method of claim 1 wherein said effective amount is about 7 mg per kilogram of mammal body weight.

7. The method of claim 1 wherein said calcein is in a water solution.

* * * * *

UNITED STATES PATENT AND TRADEMARK OFFICE
CERTIFICATE OF CORRECTION

PATENT NO. : 5,346,689
DATED : September 13, 1994
INVENTOR(S) : Peyman et al

It is certified that error appears in the above-indentified patent and that said Letters Patent is hereby corrected as shown below:

Col. 4, line 42 "Anglograms" should be --Angiograms--.

Col. 5, line 7 "anglograms" should be --angiograms--.

Col. 5, line 39 "anglograms" should be --angiograms--.

Signed and Sealed this

Fifteenth Day of November, 1994

Attest:

BRUCE LEHMAN

*Attesting Officer*     *Commissioner of Patents and Trademarks*